United States Patent [19]

Herring

[11] Patent Number: 5,041,091

[45] Date of Patent: Aug. 20, 1991

[54] KIT AND METHOD FOR HARVESTING ENDOTHELIAL CELLS AND INOCULATING A VASCULAR PROSTHESIS

[76] Inventor: Malcolm B. Herring, 1640 Walden Ct., Zionsville, Ind. 46077

[21] Appl. No.: 584,505

[22] Filed: Sep. 17, 1990

Related U.S. Application Data

[63] Continuation of Ser. No. 920,992, Oct. 20, 1986, abandoned.

[51] Int. Cl.⁵ ............................................. A61M 29/00
[52] U.S. Cl. ..................................... 604/102; 604/103
[58] Field of Search ............................... 604/96–104, 604/41, 43, 44, 45, 48, 93, 96–104, 264, 270, 275, 278, 279, 283; 600/36; 128/747, 750, 325, 344, 348.1

[56] References Cited

U.S. PATENT DOCUMENTS

| | | | |
|---|---|---|---|
| 550,238 | 11/1895 | Allen, Jr. | 604/39 |
| 871,474 | 11/1907 | Buckner | 604/99 |
| 2,642,874 | 6/1953 | Keeling | 604/102 |
| 3,916,874 | 11/1975 | Perrin | 600/36 |
| 4,108,161 | 8/1978 | Samuels et al. | 128/334 R |
| 4,211,233 | 7/1980 | Lin | 604/43 |
| 4,305,392 | 12/1981 | Chester | 604/98 |
| 4,323,072 | 4/1982 | Rosenbluth et al. | 604/275 |
| 4,601,706 | 7/1986 | Aillón | 604/102 |
| 4,610,662 | 9/1986 | Weikl et al. | 128/348.1 |
| 4,723,556 | 2/1988 | Sussman | 604/102 |
| 4,736,850 | 4/1988 | Bowman et al. | 206/370 |

Primary Examiner—C. Fred Rosenbaum
Assistant Examiner—Sharon Finkel

[57] ABSTRACT

A kit for inoculating a prosthetic vascular graft is provided having an endothelial cell harvester, a vascular graft inculator or seeder, a temperature control element, and a support structure to house each of the elements of the kit. The cell harvester included in the kit comprises a rigid rod, adapted to be inserted into a donor vein, a bulb affixed to one end of the rigid rod, the bulb having a plurality of irrigation holes, a rigid tube affixed to the bulb and communicating with the interior of the bulb, an inflatable balloon affixed to the rigid rod, and a multiple lumen flexible tube, with one lumen communicating with the inflatable balloon and at least one lumen communicating with the interior of the bulb, each of said lumens terminating in a valve member at the free end of the lumen.

A method is provided for harvesting endothelial cells from a donor vein using the cell harvester. The cell harvester is inserted into a donor vein, the vein ends are occluded, an enzyme is injected into the vein, the occlusion at one end of the vein is removed, and the enzyme and harvested endothelial cells are washed into a receptacle.

13 Claims, 5 Drawing Sheets

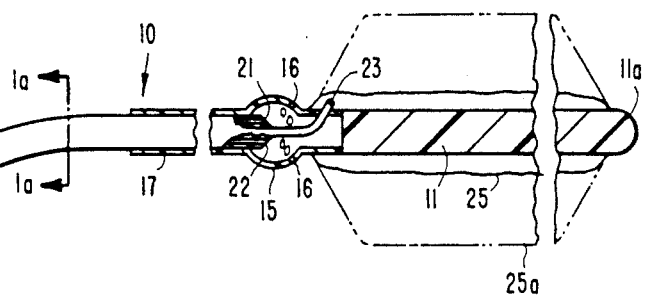
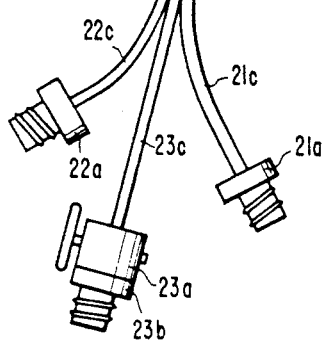
Fig.1
Fig.1a
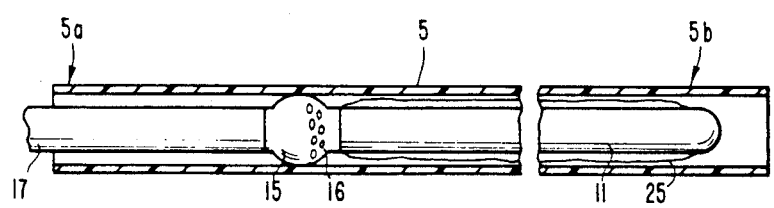
Fig.2
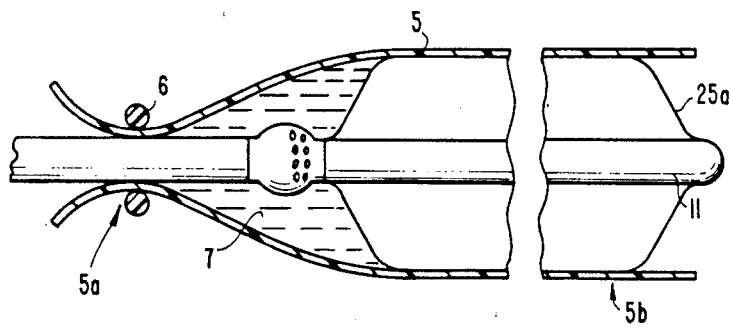
Fig.3

KIT AND METHOD FOR HARVESTING ENDOTHELIAL CELLS AND INOCULATING A VASCULAR PROSTHESIS

This application is a continuation of application Ser. No. 920,992, filed Oct. 20, 1986, now abandoned.

BACKGROUND OF THE INVENTION

1. Field of the Invention

This invention relates generally to the field of vascular prostheses and the preparation of these prostheses for implantation in the body of the patient. In particular, this invention concerns a method and kit for harvesting endothelial cells from donor blood vessel, and for inoculating the vascular prosthesis with these cells to facilitate acceptance of the prosthesis within the body.

2. Description of the Prior Art

In the practice of vascular surgery, defects in the vascular system, such as aneurysms or occlusions, are corrected by the technique of suture anastomosis, by which the affected area is excised or resected, and replaced by a prosthetic vascular graft which is implanted and sutured in place. One problem with the use of prosthetic vascular grafts is that the surface of the grafts are thrombogenic and unstable unless covered by endothelium. If blood flow through the graft is compromised, even momentarily, a complete occlusion of the graft may result. The addition of the endothelial lining produces a graft that is non-thrombogenic and is capable of repair and renewal.

The endothelial cells used to inoculate, or seed, the prosthetic vascular graft are extracted, or harvested, from a donor vein of the patient receiving the graft. In the past, the procedure for harvesting the endothelial cells involved inverting a segment of a donor vein of the patient, typically the jugular vein. In this method, the donor vein is turned "inside-out" over a rigid rod. The vein is immersed consecutively into a pair of enzyme solutions that break the bond between the single layer of endothelial cells and the underlying cells of the vein. Once the cell bonds are broken, the inverted vein is spun in medium so that the endothelial cells are separated from the vein by centrifugal force. The cells are resuspended and are used to inoculate the prosthetic graft. This procedure has been described in Stanley, Burkel, et al., *Biologic and Synthetic Vascular Prosthesis*, 1982, ch. 38 "Endothelial Seeding of Enzymatically Derived and Cultured Cells on Prosthetic Grafts".

A double enzyme process has been used to extract the endothelial cells from the donor vein. The donor vein is incubated in a first enzyme, such as trypsin, which is used to break the junctions between the endothelial cells. The vein is then immersed in a second enzyme, such as collagenase, which then infiltrates between the endothelial cells to attack the bonds with the underlying vein tissue.

One difficulty in the prior method has been that the procedure is time consuming, frequently lasting nearly two hours between extraction of the donor vein until preparation of the seeded prosthetic vascular graft for insertion into the patient. Another problem is that the cell harvesting is performed in a laboratory apart from the operating room, thus necessitating that the donor vein be transported outside the sterile environment of the O.R.

The prior method is also cumbersome in that the donor vein must be transported to the laboratory and the endothelial cell suspension must be transported back to the O.R. Inverting the donor vein and using two enzymes to extract the cells also contributes to the cumbersome nature of this method.

One purpose of the present invention is to provide a kit and a method for harvesting endothelial cells and seeding a prosthetic vascular graft that can be performed quickly and efficiently within the operating room. Another purpose is to provide a method and kit for practicing the method that is simple, leaving little room for error or contamination.

SUMMARY OF THE INVENTION

One embodiment of the kit for seeding a prosthetic vascular graft of present invention might include an endothelial cell harvester, a prosthetic vascular graft seeder, a temperature control element, and a support structure to house each of the elements of the kit.

An endothelial cell harvester in another embodiment comprises means for stabilizing a donor vessel and irrigation means for introducing a fluid into the vessel. The irrigation means in this embodiment is attached to the vessel stabilizing means.

A prosthetic vascular graft seeder in another embodiment of the present invention comprises a cover section having a flat surface and an inoculation trough projecting below the flat surface. The trough has closed ends and is adapted to accommodate a vascular prosthesis placed therein. The seeder also comprises a base section that is engaged with the cover section to support the cover section in a generally horizontal orientation. The base section has a reservoir situated beneath the inoculation trough. The reservoir substantially surrounds and is at least coextensive with the trough.

In one method of the present invention, endothelial cells are harvested from a donor vessel by first stabilizing the vessel and occluding one end of the vessel. An enzyme adapted to harvest endothelial cells is introduced into the interior of the donor vessel, after which the remaining end of the vessel is occluded. After an incubation period, the occlusion at one end of the donor vessel is removed and the enzyme and harvested endothelial cells are flushed into a receptacle.

In another method of the invention, a prosthetic vascular graft is seeded with endothelial cells by first providing an aliquot suspension of endothelial cells. The prosthetic graft is then inoculated with a portion of the aliquot suspension and the graft is placed within an inoculation trough. After the expiration of an incubation period, the graft is inoculated again with the remaining portion of the aliquot suspension. The graft is replaced into the trough and rotated longitudinally 180° from the original orientation of the graft.

BRIEF DESCRIPTION OF THE DRAWINGS

FIG. 1 is a side fragmentary view of one embodiment of the present invention showing an endothelial cell harvester.

FIG. 1A is an enlarged cross-sectional view taken at Section 1A—1A in FIG. 1, showing the triple lumen tube.

FIG. 2 is a side cutaway view of the cell harvester of FIG. 1 inserted within a donor vein and with the inflatable balloon in the uninflated condition.

FIG. 3 is a side cutaway view of a portion of the cell harvester inserted within a donor vein as shown in FIG. 2, shown with the balloon inflated.

DESCRIPTION OF THE PREFERRED EMBODIMENT

Figure 4:
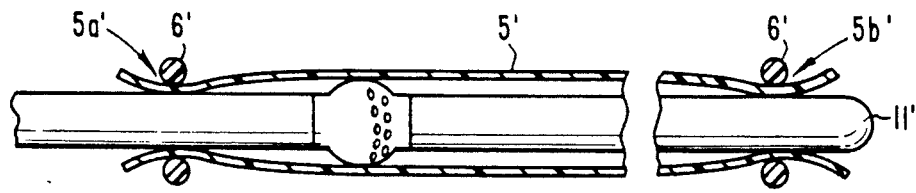
FIG. 4 is a side cutaway view of a portion of an alternative embodiment of the cell harvester inserted within a donor vein, said embodiment not having an inflatable balloon.

For the purposes of promoting an understanding of the principles of the invention, reference will now be made to the embodiments illustrated in the drawings and specific language will be used to describe the same It will nevertheless be understood that no limitation of the scope of the invention is thereby intended, such alterations and further modifications in the illustrated kit, devices and methods, and such further applications of the principles of the invention as illustrated therein being contemplated as would normally occur to one skilled in the art to which the invention relates.

In one preferred embodiment of the present invention, a kit is provided comprising an endothelial cell harvester and a prosthetic vascular graft seeder. Referring to FIG. 1, the cell harvester 10 includes a rigid rod 11 affixed to a bulb 15. The rigid rod 11 is adapted to be inserted into and support a donor vein. The rigid rod 11 has a smooth rounded free end 11a to facilitate its insertion into a donor vein without damaging the vein interior wall. The bulb 15 has a hollow interior and a plurality of irrigation holes 16 communicating through the bulb wall. The irrigation holes 16 are situated so that fluid escaping from the holes is directed toward the rigid rod 11. In one embodiment, the rigid rod has a length of 125 mm and a diameter of 2mm and the bulb 15 is circular in external cross-section, with maximum outer diameter of 3 mm. Also, the irrigation holes have a combined area of 0.71 mm².

A rigid tube 17 is attached to the bulb 15 in linear alignment opposite the rigid rod 11. The tube communicates with the interior of the bulb. A tri-lumen flexible tube 20, shown in cross-section in FIG. 1a, interfaces with the rigid tube 17 and the bulb 15. First and second lumens 21 and 22, respectively, communicate with the interior of the bulb. Tubes 21c, 22c, and 23c are confluent with lumens 21, 22, and 23, respectively, and are secured to the tri-lumen tube 20. The free ends of the tubes 21c and 22c terminate in a valve, in this case a Luer-Lok ® device 21a and 22a, respectively. Each case a Luer-Lok ® device is adapted to threadedly engage syringe, not shown in the figure.

A balloon 25 is affixed to the ends of the rigid rod 11 so that the balloon circumferentially surrounds the rod. A third lumen 23 in the tri-lumen flexible tube 20 passes through the rigid tube 17 and bulb 15 and communicates with the interior of the balloon 25. The free end of the tube 23c terminates in an inflation port assembly, in this case comprising a stopcock valve 23a and a Luer-Lok ® device 23b. The Luer Lock device is adapted to threadedly engage a syringe, not shown in the figure. The balloon 25 has a normally deflated condition, shown in solid lines, and is adapted to be inserted into a donor vein. In an inflated configuration 25a, shown in phantom in FIG. 1, the balloon 25 contacts the interior of the donor vein. The balloon 25 is elastomeric and is adapted, when inflated, to assume the distended shape and diameter of the vein. In a specific application of applicants' invention the inflated diameter of the balloon is 10 mm.

The rigid rod, bulb, and rigid tube of the harvester are composed of a plastic, such as polyvinyl chloride. The balloon material is reinforced latex, but can be some other similar material capable of inflating and conforming to a vein wall.

The cell harvester 10 is used in the method of the present invention. A donor vein, typically a jugular vein, is extracted from the patient. The rigid rod 11, with the balloon 25 affixed thereon, is inserted into the donor vein 5 until the bulb 15 and at least a portion of the rigid tube 17 are within the donor vein, as shown in FIG. 2. End 5a of the vein is occluded or tied off against the rigid tube 17 by a ligature 6, as shown in the FIG. 3.

Once end 5a of the vein is occluded, an enzyme solution adapted for harvesting endothelial cells is injected by syringe, not shown in the figures, through the Luer-Lok ® 21a and the first lumen 21 into the bulb 15. In one version of the present method, the enzyme is collagenase. The enzyme solution 7 passes from the bulb 15, through the plurality of irrigation holes 16 into the vein 5. After the enzyme solution has been introduced into the vein, the balloon 25 is inflated, thereby distending and occluding the vein 5 at end 5b, as shown in FIG. 3, and trapping the enzyme within the vein. A certain amount of the enzyme solution is trapped between the inflated balloon 25a and the vein interior wall. The balloon is inflated by opening the stopcock valve 23a and engaging a syringe with the Luer-Lok ® device 23b. The contents of the syringe, typically air, is injected into the balloon, after which the stopcock valve is closed.

In another version of the present invention, illustrated in FIG. 4, the balloon 25 is eliminated from the cell harvester along with the third lumen 23, the stopcock 23a and the Luer Lock 23b. The ends 5a' and 5b' of the vein 5' are occluded around the rigid rod 11' using a ligature 6' as applied at end 5a of the vein in FIG. 3.

The enzyme is allowed to incubate within the vein for a period of time necessary to break the bonds between the endothelial cells and the underlying cell layer. In applicants' procedures to date, the enzyme collagenase has been permitted to digest the endothelial attachments for about 10 minutes. It was found that maintaining a 37° C. temperature in the vein during incubation, in combination with the enzyme and calibrated digestion time, produced an excellent yield of endothelial cells.

Figure 5:
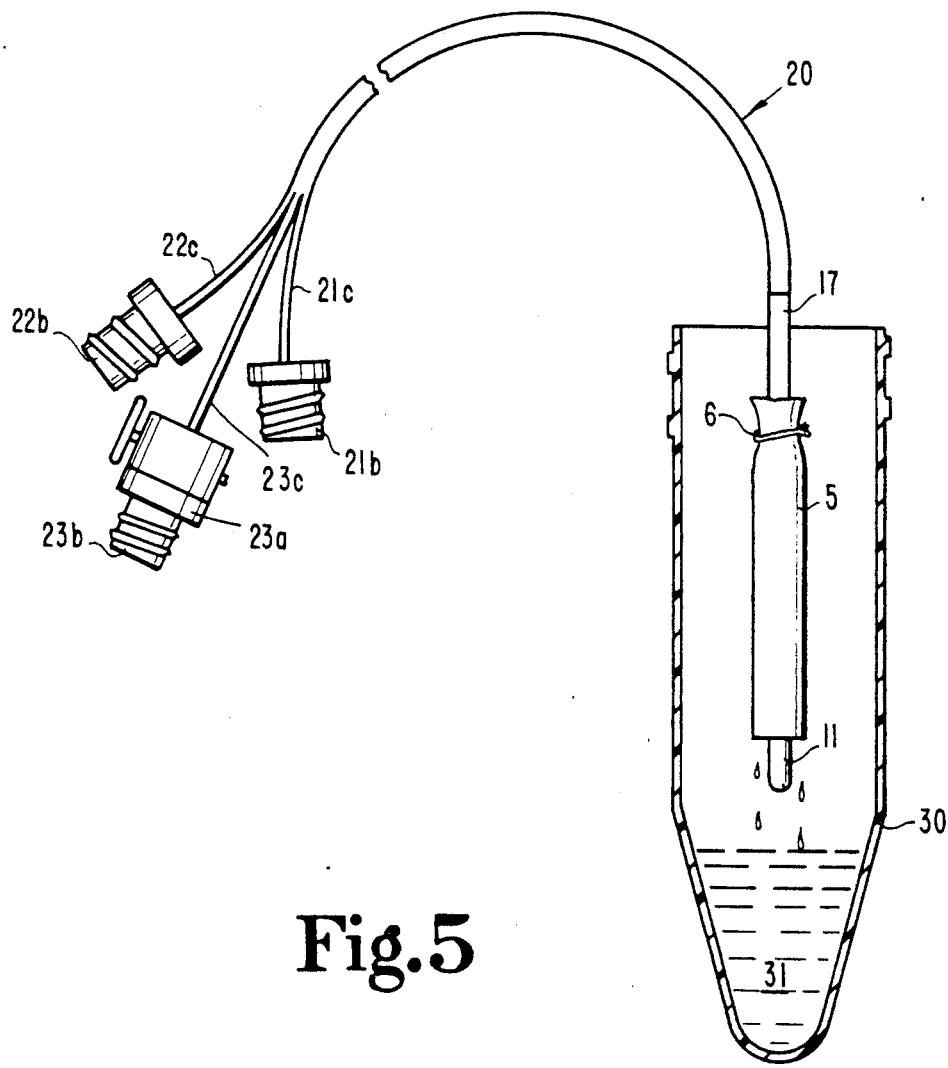
FIG. 5 is a side cutaway view illustrating a step in a method of one embodiment in which the cell harvester is suspended vertically within a centrifuge tube.

Once the incubation period expires, the donor vein is placed within a receptacle, such as a centrifuge tube 30 shown in FIG. 5, and the balloon 25 is deflated by opening the stopcock valve 23a and either drawing the air in the balloon into the syringe, or disengaging the syringe from the Luer-Lok ® device 23b and allowing the air to escape naturally. With the balloon deflated and with the ligature 6 still occluding the end 5a of the vein, a culture medium is injected by syringe through the Luer Lok ® device 22a, tube 22c and second lumen 22 into the bulb 15. It is understood that the culture medium could be injected through Luer-Lok ® device 21a, tube 21c and lumen 21 since this lumen also communicates with the bulb 15. In this instance, lumen 22 can be eliminated from cell harvester 10. One advantage, however, of the second lumen 22 is that there is no need to disengage the syringe containing the enzyme solution from Luer-Lok ® device 21a in order to engage a syringe containing the culture medium. Separate lumens for the enzyme and washing solutions facilitate the procedure and reduces the risk of accident.

The culture medium strips or washes the enzyme and endothelial cells from the interior surface of the vein. The resulting effluent cell suspension 31 flows into the centrifuge tube 30, as shown in FIG. 5. In one version of the method of the present embodiment, the centrifuge tube, donor vein and cell harvester are supported in a vertical position during the final phases of the cell harvesting. In this position, the effluent flows by gravity into the centrifuge tube. The centrifuge tube containing the effluent is then placed in a centrifuge to separate the endothelial cells from the enzyme solution and culture medium. The resulting pellet of endothelial cells is resuspended in a culture medium for inoculation into the prosthetic vascular graft. The culture medium may be, for example, M-199.

One advantage of the cell harvester and method of cell harvesting of the present invention is that the amount of time required to harvest endothelial cells is greatly reduced. In applicants' procedures to date, the cell harvesting process typically has taken about 20 minutes from extraction of the donor vein to production of an aliquot solution of endothelial cells and culture medium. In the present method, the donor vein need not be inverted. The harvester used in the present method is a closed system, thereby limiting airborne bacterial contamination.

Another advantage is that the entire procedure can be practiced in the operating room during a surgical operation. The procedure disclosed in the present invention is easy to perform in the O.R. because the donor vein is not transported between receptacles.

The procedure is further simplified because it is not necessary to utilize two enzyme solutions to extract the endothelial cells. The single enzyme procedure of the present invention reduces the risk of confusion between enzymes, a particularly important feature in the tense environment of a surgical procedure. Tests by applicants have indicated that the distension of the donor vein accomplished by the inflation of the balloon 25 may have a tendency to physically break the cell junctions in the layer of endothelial cells, thereby alleviating the need for exposure to an enzyme, such as trypsin, to chemically break the cell junctions. Thus, use of two enzymes is also not necessary in order to effectively extract the endothelial cells.

Figure 6:
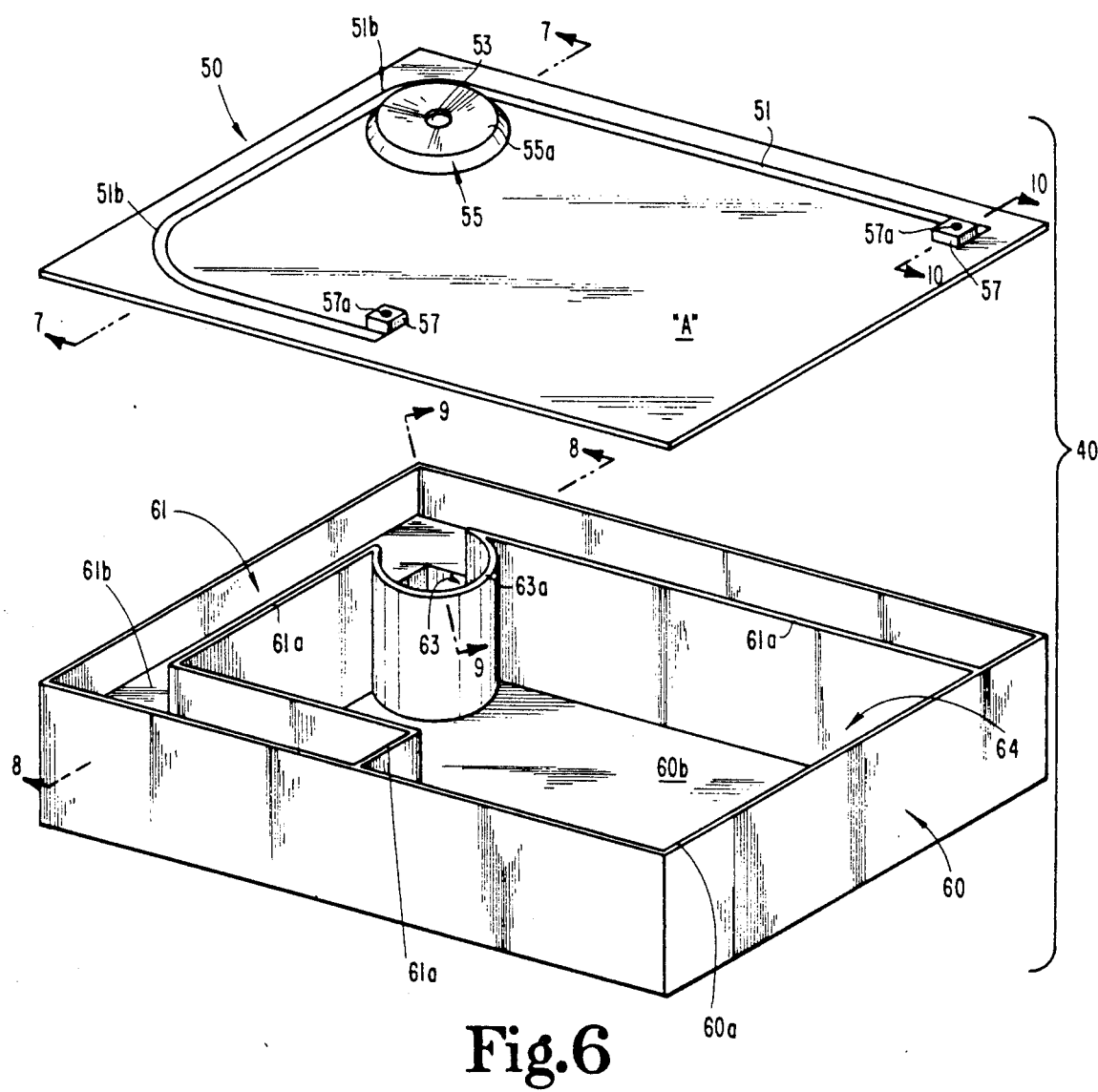
FIG. 6 is an exploded orthographic view of one embodiment of the present invention showing a prosthetic vascular graft seeder.
Figure 7:
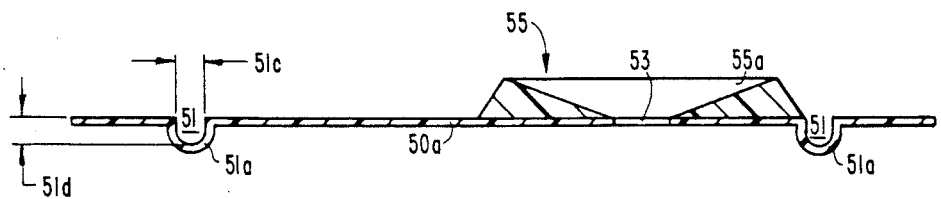
FIG. 7 is a cross-sectional view of the cover section taken at Section 7—7 in FIG. 6 and viewed in the direction of the arrows showing the inoculation trough, the opening and the shoulder.

Referring to the exploded view in FIG. 6, the seeder 40 includes a cover section 50 and a base section 60. The cover section 50 consists of a generally rectangular flat plate 50a in which a trough 51 is indented. The trough 51 is formed adjacent a substantial length of the perimeter of the plate 50a. The length of the trough is equivalent to the typical maximum length of a prosthetic vascular graft, usually 80-90 cm. Curves 51b in the trough are calibrated to accommodate the "radius potential" of a typical prosthetic vascular graft, so that a graft situated within the trough 51 at a curve 51b will not kink or crimp. For a common graft having a radius potential 7-8 cm., the radius of curvature of the curves 51b is 7-8 cm. The trough 51 is adapted to accommodate a typical diameter graft therein. The trough wall 51a, shown in FIG. 7, is half-circular in cross section with tangent parallel upper sides to accept the prosthetic graft. The trough cross-section is configured to reduce the likelihood of the graft rolling about its longitudinal axis within the trough and, consequently, to reduce the likelihood of disruption of the cell attachment process or alteration of the cell distribution in the graft. One configuration that produces this desirable effect is a trough, the width of which is sized only slightly larger than the graft diameter. For a typical graft, the trough diameter 51c measures 1 cm, and the trough depth 51d is 1 cm. The longitudinal axis of the half-circular portion of the trough 51 is in a plane that is generally parallel with the flat plate 50a so that the trough will be horizontal when the seeder is in use. Keeping the trough 51 in a horizontal orientation during use ensures that the prosthetic vascular graft will be evenly and thoroughly seeded by the endothelial cell suspension.

The flat plate 50a has an circular opening 53 near one corner of the plate. The diameter of the opening 53 is sufficient to accommodate at least one centrifuge tube inserted therethrough. A shoulder 55 surrounds the opening 53 and is affixed to the plate 50a. The shoulder 55 has a frusto-conical surface 55a to direct fluid contacting the shoulder through the opening 53, thus preventing the fluid from entering into other areas of the seeder. An equipment area "A" occupies the remainder of the surface of the flat plate. A cell harvester, a prosthetic vascular graft, and other medical equipment may be placed in this area "A" during use of the seeder.

Figure 8:
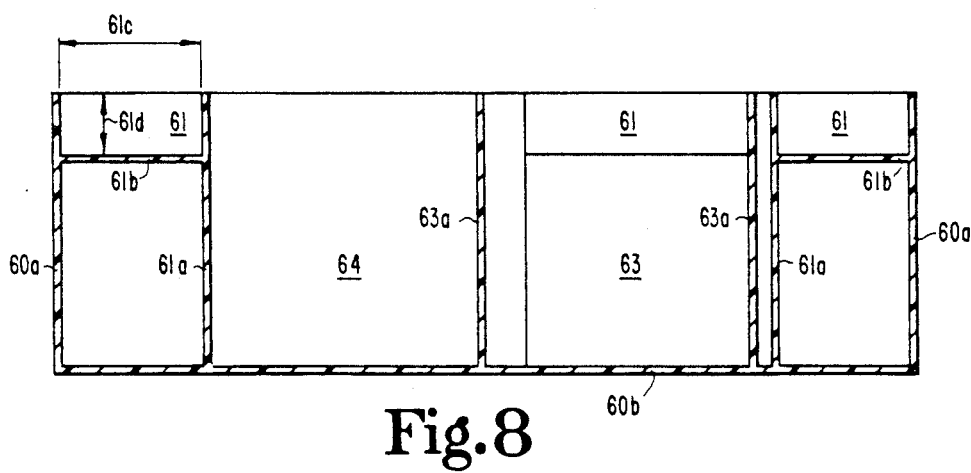
FIG. 8 is a cross-sectional view of the base section taken at Section 8—8 in FIG. 6 and viewed in the direction of the arrows showing the first, second, and third reservoirs.

Returning to the exploded view in FIG. 6 the base section 60 comprises a generally rectangular perimetrical wall 60a and a bottom Wall 60b. A first reservoir 61 is formed inboard of perimetrical wall 60a. The first reservoir 61 has a side perimetrical wall 61a and a bottom wall 61b, and is generally rectangular in cross-section, as shown in FIG. 8. The depth of the first reservoir 61 is calibrated to accept the trough 51 and to allow a fluid placed in the first reservoir to substantially surround the trough. In one specific version, the reservoir measures 5 cm in width, dimension 61c, and 3 cm in depth, dimension 61d. The first reservoir 61 follows the path of the trough 51 so that the entire length of the trough is encompassed within the first reservoir 61. The first reservoir 61 is slightly longer than the trough 51.

Figure 9:
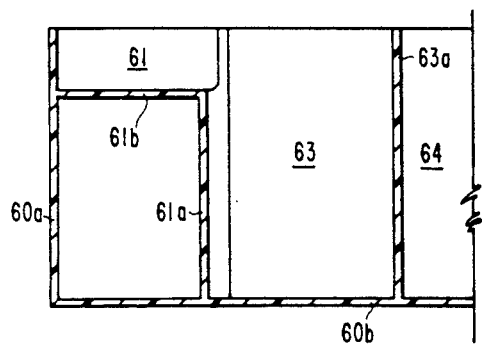
FIG. 9 is a cross-sectional view of the base section taken at Section 9—9 of FIG. 6 and viewed in the direction of the arrows, showing the first, second and third reservoirs.

A second reservoir 63 is formed by the bottom wall 60b of the base section and a part-cylindrical wall 63a. The dimensions of the second reservoir, radius and depth, are designed to accommodate at least one centrifuge tube placed therein. The second reservoir 63 is situated in the base section 60 so that the opening 53 in the upper section 50 empties directly into the reservoir when the two seeder sections are engaged The second reservoir 63 is confluent with the first reservoir 61, as shown in FIGS. 6 and 9.

An overflow reservoir 64 is formed by a portion of perimetrical wall 60a, bottom wall 60b, perimetrical wall 61a, and part-cylindrical wall 63a.

Figure 10:
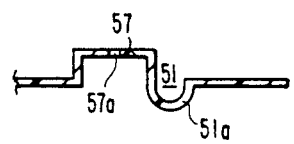
FIG. 10 is a cross-sectional view of the cover section taken at Section 10—10 of FIG. 6 and viewed in the direction of the arrows, showing the inoculation trough and an overflow vent.
Figure 11:
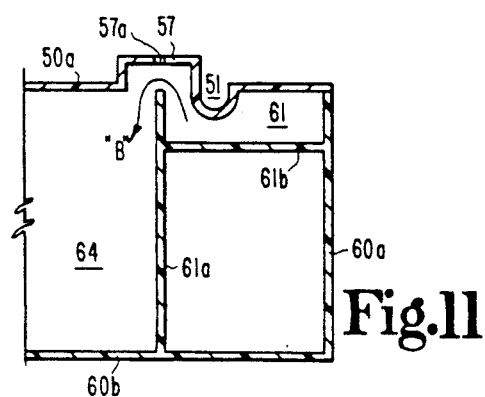
FIG. 11 is a cross-sectional view of the cover section joined to the base section as viewed in FIG. 10. showing the flow path between the first and third reservoirs through the overflow vent.

When the seeder is fully assembled, the free edges of the walls 60a, 61a and 63a tightly abut and are sealingly secured to the underside of the flat plate 50a to form a generally leak-proof seal for the first, second and overflow reservoirs 61. 63 and 64 respectively. In the use of the seeder, the first and second reservoirs 61 and 63, respectively, are filled with a fluid, and any overflow from these reservoirs is directed into the overflow reservoir 64. A pair of vents 57 are formed in the flat plate 50a at each end of the trough 51. The vents 57 are inboard of the trough, as shown in FIGS. 6 and 10, and are situated so that a flow path, represented by arrow "B" in FIG. 11, is formed from the first reservoir 61, over the first reservoir perimetrical wall 61a, and into the overflow reservoir 64. The vents 57 each have an air bleed hole 57a to allow air to escape when displaced by fluid poured into the reservoirs.

The seeding technique of the invention has been used by applicants on polytetrafluroethylene (PTFE) grafts, such as grafts composed of a material sold commercially under the tradename GORE-TEX by W. L. Gore and Associates. The PTFE graft is prepared for seeding by first pre-clotting the graft to seal the graft interstices. An aliquot suspension of harvested endothelial cells is then prepared.

A quantity of a pre-warmed fluid, typically sterile saline at 37° C. is poured through the opening 53 into the first and second reservoirs 61 and 63 respectively. The shoulder 55 around the opening 53 helps prevent fluid from being accidentally poured into the equipment area "A" on the flat plate 50a. The reservoirs 61 and 63 are filled with a pre-measured quantity of sterile saline, or they can be filled until fluid overflows through a vent 57 into the overflow reservoir 64.

Figure 13:
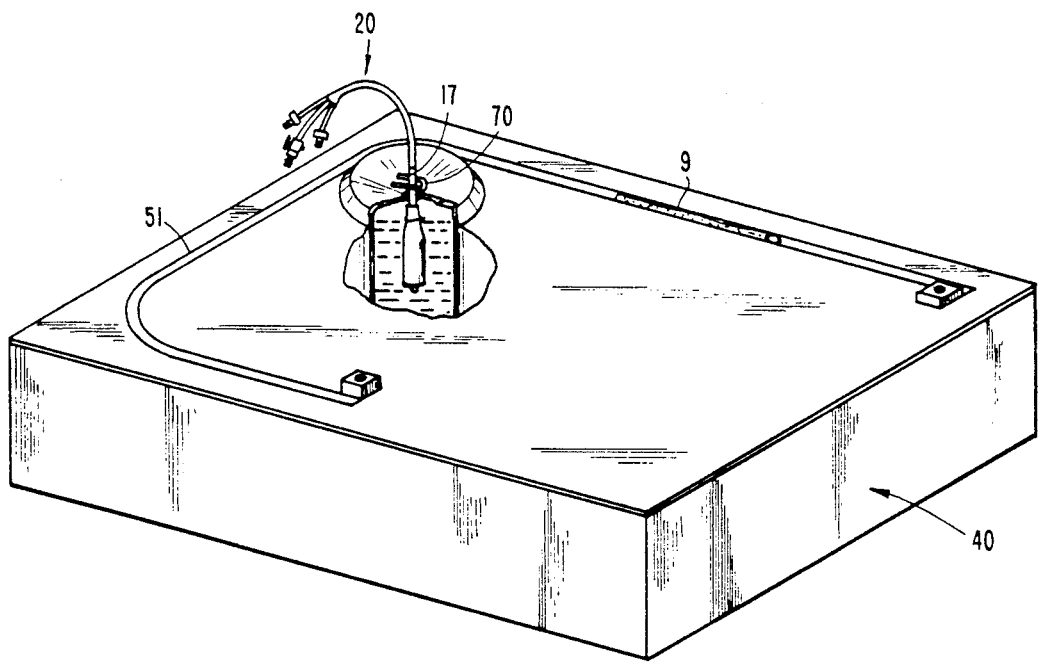
FIG. 13 is an perspective view illustrating a step in a method of one embodiment in which a prosthetic vascular graft and a cell harvester are situated within the prosthetic vascular graft seeder.

The pre-clotted prosthetic graft is inoculated with the aliquot solution of endothelial cells, typically by syringe. In applicants' procedures to date, the graft is inoculated with half of the initial aliquot. As shown in FIG. 13, the graft 9 is then placed in the inoculation trough 51 for an incubation period to allow the endothelial cells to properly adhere to the PTFE surface. The incubation period in the procedures to date has been about 10 minutes. After the incubation period, the graft is inoculated with the remaining portion of the aliquot. The graft is again placed in the trough 51 and rotated 180° longitudinally from the orientation in the first inoculation period to ensure that the endothelial cells are uniformly distributed about the graft circumference. The 180° rotation places that portion of the graft facing down that was facing up in the initial incubation period. At the expiration of the final incubation period, the PTFE graft can be sutured into place.

The seeder provides adequate temperature control of the graft during incubation of the endothelial cells within the graft. Maintaining the graft near 37° C. enhances the induction of the endothelial cells into the graft. The pre-warmed saline solution keeps the graft at or near the desired temperature, even though the operating room temperature is as low as 19° C., as is typical during a surgical operation. Since the elapsed time of the graft seeding process is generally less than 30 minutes, the saline solution in the seeder reservoirs experiences only a slight drop in temperature.

One advantage of the prosthetic vascular graft seeder and method of using the seeder disclosed herein is that the graft seeding process can be quickly and easily performed in the operating room. The use of a pre-warmed saline solution as a thermal medium is simple and readily accessible in an operating room environment. Maintaining the graft at a nearly constant 37° C. temperature enhances the incubation of the cells. The simplicity of the method and use of the seeder greatly reduces the risk of accidents. The configuration of the seeder inoculation trough prevents any rolling of the graft, thereby ensuring a uniform seeding of endothelial cells throughout the entire graft.

Figure 12:
FIG. 12 is a top view of a stabilizer clip adapted to support the cell harvester of the present invention.

The second reservoir 63 of the seeder is used to receive the cell harvester during incubation or cell digesting process. Suspending the cell harvester vertically in the pre-warmed saline solution allows the enzymatic reaction to occur at an optimal temperature, thereby improving the efficiency of the harvesting process and increasing the yield of endothelial cells. During the harvesting process, the harvester 10 is held in position by a thin U-shaped stabilizer clip 70 of FIG. 12. Referring to FIG. 13, the clip 70 engages the harvester 10 adjacent the bulb 15 in the vicinity of the ligature 6. The clip extends horizontally and rests upon the frusto-conical surface 55a of the shoulder 55 on the seeder 40, thereby suspending the harvester 10 in the saline solution occupying the second reservoir 63.

The kit in one embodiment of the present invention comprises the cell harvester and prosthetic vascular graft seeder as described above. The kit is provided as a complete self-contained unit, available in the operating room when a vascular replacement is required. The harvester, stabilizer clip, enzyme and washing solutions, syringes, and other medical instruments are housed in equipment area "A" of the seeder. The elements of the kit can be protected from jostling by placing them in a recess or plurality of shaped recesses added to the equipment area. The syringes can be filled with pre-measured quantities of the enzyme and washing solutions and labelled accordingly to facilitate the method of use of the cell harvester described in the present invention. The components of kit are sterilized for safe use in the sterile environment of the operating room. The complete kit is then wrapped with an impervious paper drape and sealed with a plastic liner to protect the sterilized kit.

An advantage of the kit is that it keeps all the necessary elements to prepare a prosthetic graft in one easily accessible location. The kit can be used in the operating room during the surgical operation quickly and efficiently. The elements of the kit and their method of use is simple so that there exists little danger of confusion and accident during the cell harvesting or seeding procedures. The kit and methods of the present invention obviates the need for interim steps involving a laboratory or activity outside the O.R. In applicants' procedures to date, use of the kit and methods described above has substantially shortened the total time of the operation. The total time required for preparing the vascular graft, from removal of the donor vein to immediately before the graft is sutured in place, has been only 35–40 minutes. Use of the kit and method of this invention represents an improvement over the 1–2 hour total graft preparation time endured in prior techniques. The obvious benefits of this reduction in time are obviously significant in the environment of the operating room.

While the invention has been illustrated and described in detail in the drawings and foregoing description, the same is to be considered as illustrative and not restrictive in character. It is understood that only the preferred embodiments have been shown and described and that all changes and modifications that come within the spirit of the invention are desired to be protected.

What is claimed is:

1. A cell harvester for harvesting endothelial cells from a donor vein or blood vessel comprising:
   means for stabilizing a vessel; and
   irrigation means for introducing a fluid into said vessel, said irrigation means being attached to said vessel stabilizing means and including;
   a bulb defining an interior volume and having a plurality of irrigation holes, said bulb being adapted to be inserted into said vessel;
   a rigid tube attached to said bulb at a first end of said rigid tube and communicating with said interior volume of the bulb, said rigid tube being adapted to be inserted into said vessel;
   a first lumen passing through said rigid tube and communicating with said interior volume of said bulb at a first end of said first lumen; and
   first valve means at a second end of said first lumen.

2. The cell harvester of claim 1, wherein said vessel stabilizing means comprises:
   a rigid rod adapted to be inserted into said vessel:
   said rigid rod being connected to said bulb in opposing orientation to said rigid tube and situated so that said rigid rod and said rigid tube are in linear alignment.

3. The cell harvester of claim 1, wherein said irrigation means further comprises:
   a second lumen passing through said rigid tube and communicating with said interior volume of said bulb at a first end of said second lumen; and
   second valve means at a second end of said second lumen.

4. The cell harvester of claim 3, wherein;
   said first and second lumen are integral over a substantial portion of the length of each of said first and second lumen;
   said first valve means comprises first means for engaging a syringe; and
   said second valve means comprises second means for engaging a syringe.

5. A cell harvester for harvesting endothelial cells from a donor vessel, comprising:
   means for stabilizing a vessel;
   means, associated with said means for stabilizing, for occluding the vessel for collecting harvested cells within the vessel; and
   irrigation means for introducing fluid into the vessel, said irrigation means being attached to said vessel stabilizing means, wherein said irrigation means includes;
   a bulb defining an interior volume and having a plurality of irrigation holes, said bulb being adapted to be inserted into the vessel;
   a rigid tube attached to said bulb at a first end of said rigid tube and communicating with said interior volume of the bulb, said rigid tube being adapted to be inserted into the vessel;
   a first lumen passing through said rigid tube and communicating with said interior volume of said bulb at a first end of said first lumen; and
   first valve means at a second end of said first lumen.

6. The cell harvester of claim 5, wherein said vessel occluding means includes:
   an inflatable balloon affixed to the vessel stabilizing means, said balloon being adapted to be inserted into the vessel when in a deflated condition and to distend the vessel when in an inflated condition; and
   a second lumen communicating with said balloon at a first end of said second lumen, whereby a fluid may be admitted under pressure into said balloon.

7. The cell harvester of claim 6, wherein said vessel stabilizing means includes a rigid rod adapted to be inserted into the vessel; and
   said inflatable balloon circumferentially surrounds said rigid rod and extends substantially along the length of said rigid rod.

8. The cell harvester of claim 7, wherein said inflatable balloon is composed of an elastomeric material capable of conforming to a distended configuration of said vessel when said balloon is inflated.

9. The cell harvester of claim 7, wherein said rigid tube is connected to said bulb in opposing orientation to said rigid rod and situated so that said rigid tube and said rigid rod are in linear alignment.

10. The cell harvester of claim 6, wherein: said second lumen passed through said rigid tube and said interior volume of said bulb; and
    said means for occluding further comprises inflation port means affixed to a second end of said second lumen.

11. The cell harvester of claim 10, wherein; said inflation port means comprises:
    a stopcock device affixed to said second end of said second lumen;
    first means for engaging a syringe adapted to engage said stopcock device in fluid communication therewith; and
    said first valve means comprises second means for engaging a syringe.

12. The cell harvester of claim 10, wherein said irrigation means further comprises:
    a third lumen passing through said rigid tube and communicating with said interior Volume of said bulb at a first end of said third lumen; and
    second valve means at a second end of said third lumen, said second valve means being adapted to engage a syringe.

13. The cell harvester of claim 12, wherein said first, second and third lumens are integral over a substantial portion of the length of each of said first, second and third lumens.

* * * * *